United States Patent [19]

De Harde et al.

[11] Patent Number: 5,215,534
[45] Date of Patent: Jun. 1, 1993

[54] SAFETY SYRINGE SYSTEM

[76] Inventors: Lawrence De Harde; Michael DeHarde, both of 2100 Montes Quieu, Chalmette, La. 70043

[21] Appl. No.: 801,669

[22] Filed: Dec. 2, 1991

[51] Int. Cl.⁵ ............................................. A61M 5/32
[52] U.S. Cl. ..................... 604/198; 604/110; 604/192; 128/919
[58] Field of Search ............... 604/110, 118, 192, 196, 604/198, 197, 187, 117

[56] References Cited

U.S. PATENT DOCUMENTS

| | | | |
|---|---|---|---|
| 2,559,474 | 7/1951 | Son | 604/192 |
| 2,854,976 | 10/1958 | Heydrich | 604/192 |
| 4,702,738 | 10/1987 | Spencer | 604/198 |
| 4,725,267 | 2/1988 | Viallancourt | 604/192 |
| 4,790,828 | 12/1988 | Dombrowski et al. | 604/198 |
| 4,804,371 | 4/1989 | Vaillancourt | 604/198 |
| 4,813,940 | 3/1989 | Parry | 604/198 |
| 4,838,863 | 6/1989 | Allard et al. | 604/110 |
| 4,846,796 | 7/1989 | Carrell et al. | 604/110 |
| 4,850,968 | 7/1989 | Romano | 604/110 |
| 4,861,338 | 8/1989 | Mathiesen et al. | 604/110 |
| 4,863,434 | 9/1989 | Bayless | 604/198 |
| 4,887,998 | 12/1989 | Martin et al. | 604/110 |
| 4,892,521 | 1/1990 | Loico et al. | 604/192 |
| 4,894,055 | 1/1990 | Sudnak | 604/198 |
| 4,908,023 | 3/1990 | Yuen | 604/118 |
| 4,915,696 | 4/1990 | Flinn | 604/192 |
| 4,921,486 | 5/1990 | DeChellis et al. | 604/110 |
| 4,932,940 | 6/1990 | Walker et al. | 604/110 |
| 4,936,830 | 6/1990 | Verlier | 604/110 |
| 4,955,868 | 9/1990 | Klein | 604/198 |
| 4,966,593 | 10/1990 | Lennox | 604/198 |
| 4,986,818 | 2/1991 | Imbert et al. | 604/192 |
| 4,994,046 | 2/1991 | Wesson et al. | 604/198 |
| 5,026,353 | 6/1991 | Bartman | 604/192 |

Primary Examiner—C. Fred Rosenbaum
Assistant Examiner—Manuel Mendez
Attorney, Agent, or Firm—Joseph T. Regard, Ltd.

[57] ABSTRACT

A system for preventing needle stick or re-use of unsterile hypodermic needles or the like. The hypodermic syringe includes a spring biased, locking push button apparatus exterior to the plunger, which communicates with a locking safety sheath situated at the base of the hypodermic needle prior to activation. The safety sheath is in sliding, longitudinal communication about the needle and is activated to its sheathing position by urging a push button on the locking push button structure in the direction of the needle, directing the sheath from about the base of the needle to over the tip of the needle. Upon communication with the tip, the safety sheath deploys a locking hatch, preventing the urging of the sheath back to the base, and rendering the needle un-reusable. The locking apparatus of the invention operates independently of the syringe plunger, allowing the drawing and injection of fluids without interference, and is sheathed in its locking position only upon the independent urging of the push button, "clicking" the sheath into a locked position.

7 Claims, 4 Drawing Sheets

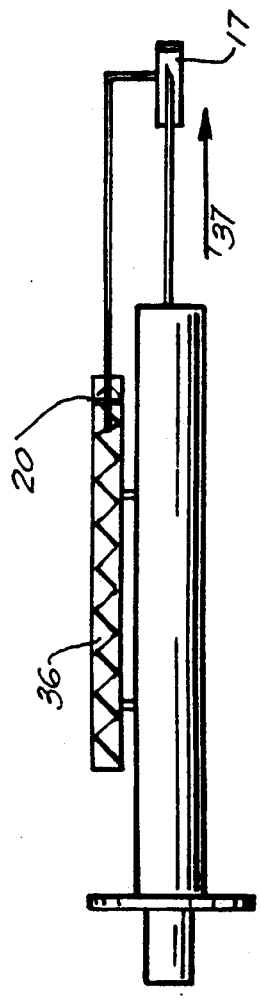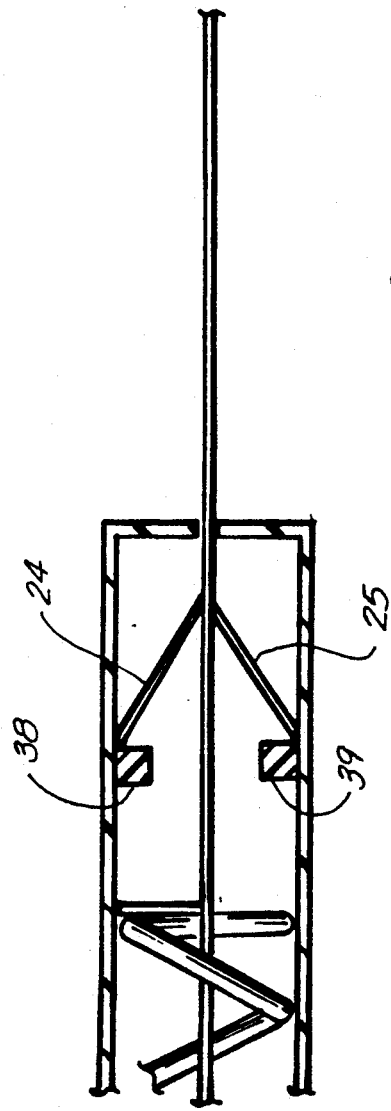

SAFETY SYRINGE SYSTEM

BACKGROUND OF INVENTION

1. Field of Invention

The present invention relates to apparatus for preventing infection from unsterile hypodermic needles or the like, and more particularly to a system for preventing needle stick or re-use of unsterile hypodermic needles or like items.

The present invention teaches in its preferred embodiment a hypodermic syringe wherein there is included a spring biased, locking push button apparatus exterior to the syringe plunger which communicates with a locking safety sheath situated at the base of the hypodermic needle prior to activation.

The safety sheath is in sliding, longitudinal communication about the needle, and is activated to its sheathing position by urging a push button on the locking push button structure in the direction of the needle, directing the sheath from about the base of the needle to over the tip of the needle. Upon communication with the tip, the safety sheath deploys a locking hatch, preventing the urging of the sheath back to the base, and rendering the needle thereafter un-reusable.

The locking apparatus of the present invention preferably operates independently of the syringe plunger, allowing the drawing and injection of fluids without interference, and is sheathed in locking position only upon the independent urging of the push button, "clicking" the sheath into a locked position.

2. Prior Art and General Background

While the prior art may teach a plurality of various devices configured to protect against needle sticks, none teach or contemplate the system as contemplated in the present invention, wherein there is provided redundant locking as a "fail-safe" apparatus.

Since the early 1980's it has been recognized that instruments which come into contact with human tissue fluids can comprise biohazards, particularly when those instruments come into contact with HIV, hepatitis, and other tissue infected with contagion.

Further, it has been recognized that the sharing and re-usage of disposable needles has transmitted HIV among intravenous drug users.

Consequently, there has evolved a plethora of redesigns of existing hypodermic syringes and related devices, wherein there has been incorporated features to prevent infection and, in the case of disposable systems, reuse.

Often, the distraction surrounding a medical emergency or like situation may result in used syringes not being identified as being particularly contaminated. This could result in the re-use of the syringe by a medical professional and potential contamination resulting therefrom.

Additionally, if the syringe is not properly disposed of, an addict may thereafter utilize it to administer illegal drugs to himself and others, spreading the virus, bacteria, disease, or anything else which may be present on the point and shaft of the hollow metal needle.

It is for this reason that an easily operated, consistent and tamper proof, syringe needle capping system is needed, so that the utilized needle may be automatically capped immediately after use, even in the heat of a medical emergency, without distraction and in a consistent and unfailing manner.

A list of prior patents which may be of interest is presented below:

| Patent No. | Patentee(s) | Issue Date |
|---|---|---|
| 4,702,738 | | |
| 4,725,267 | Vaillancourt | 02/16/88 |
| 4,790,828 | Dombrowski et al | 12/13/88 |
| 4,804,371 | Vaillancourt | 02/14/89 |
| 4,813,940 | Parry | 03/21/89 |
| 4,838,863 | Allard et al | 06/13/89 |
| 4,846,796 | Carrell et al | 07/11/89 |
| 4,850,968 | Romano | 07/25/89 |
| 4,861,338 | Mathiesen et al | 08/29/89 |
| 4,863,434 | Bayless | 09/05/89 |
| 4,887,998 | Martin et al | 12/19/89 |
| 4,894,055 | Sudnak | 01/16/90 |
| 4,908,023 | Yuen | 03/13/90 |
| 4,921,486 | DeChellis et al | 05/01/90 |
| 4,932,940 | Walker et al | 06/12/90 |
| 4,936,830 | Verlier | 06/26/90 |
| 4,955,868 | Klein | 09/11/90 |
| 4,966,593 | Lennox | 10/30/90 |
| 4,986,818 | | |
| 4,994,046 | | |
| 5,026,353 | Bartman | 06/25/91 |

U.S. Pat. No. 4,702,738 addresses the problem of inadvertent pricks, but the safety is easily manipulated once the system is locked by manipulating the spring force, easily overcoming it by hand. Further, the difficulties in performing the basic functions of using the syringe are increased by the need for holding the shield handle during injection.

U.S. Pat. No. 4,725,267 addresses the problem of inadvertent pricks by covering the point of the needle, but activating it requires the operator to work in the area of the point of the needle, increasing the potential contamination risk simply to cover the needle. Further, the cover could be forced back, exposing the needle, potentially causing a prick.

U.S. Pat. No. 4,790,828, issued in 1988, teaches a "Self-capping Needle Assembly", wherein in FIGS. 1, 2 and 6, there is contemplated a locking needle capping assembly utilizing biased blockage means, albeit distinguishable in operation and design from that contemplated by the present invention. Namely, the activation system which must be manually lifted in the '828 system is more cumbersome to operate with one hand and could actually encourage needle stick, versus the present invention, which contemplates a push-button system wherein there is a lesser chance for needle stick during the activation of the capping mechanism.

U.S. Pat. No. 4,804,371 addresses the problem of inadvertent pricks by covering the needle, but can be pushed out of the way if one desires to overcome the system, thereby failing to prevent re-use.

U.S. Pat. No. 4,994,046, issued in 1991, discloses a "Needle Guard for Syringe", wherein there is taught a side mounted apparatus for controlling the shield means, albeit completely distinguishable in form and operation from the present invention.

U.S. Pat. No. 4,863,434, issued in 1989 describes an "automatic needle sheath for disposable syringe" wherein a needle capping assembly is disclosed (note FIG. "A"), offering biased blocking members to cover the needle. However, the '434 patent fails to contemplate an efficient, inexpensive, and safe system as taught in the present invention.

U.S. Pat. No. 4,936,830 addresses the problem of inadvertent pricks and reuse, but works only on pre-filled syringes.

U.S. Pat. No. 4,986,818, issued Jan. 22, 1991, and U.S. Pat. No. 4,990,141, issued Feb. 5, 1991, also teach single use syringes utilizing a type of safety capping assembly again distinguishable from the present invention, but nonetheless pertinent with respect to the generalized concept of a single use syringe system.

Finally, U.S. Pat. No. 5,026,353 issued Jun. 25, 1991 teaches a "multi-chamber safety syringe", contemplating a rather bulky, complicated, and expensive system for preventing needle stick, wherein there is taught essentially the incorporation of dual spring biased reciprocating pistons on opposing sides of the syringe to force forward a capping assembly.

As taught, the device of the '353 patent may not only be considered impractical, but also does not teach a safe locking mechanism over the needle. In fact, as the capping system is apparently contemplated, the cap is not locked in place over the needle and may in fact slide out of the needle cap, if the cap is urged towards the base of the needle, exposing it. Therefore, if one were to bump or sit atop the cap, the cap could slide back, sticking and potentially infecting that person.

3. General, Summary Discussion of the Invention

Although the prior discussed patents disclose a plethora of various needle capping systems, none teach or contemplate the reliable, inexpensive, and easily operated system of the present invention.

As may be discerned by a review of the above, one can understand why so few systems for preventing needle stick have been commercially successful in the marketplace.

Literally dozens of various apparatus configurations have been presented to prevent needle stick or syringe re-use, but all have their flaws, particularly with regard to ease of use, reliability, safety and cost.

The present system not only provides all of the above, but does so in a system which is less complicated than most of those contemplated in the prior art.

Unlike the prior art, the present invention provides a simple system for implementing a needle cap after use which is redundant, providing locking with regard to the needle cap once in the capping position, as well as a locking system in the initiating mechanism. This is done in an easy, push-button system designed to be literally fool proof and tamper proof.

The present invention contemplates in its preferred embodiment a plunger-type syringe and needle arrangement, with a side mounted, initiating mechanism in longitudinal communication with a capping or protective cover mechanism. Both the capping mechanism and protective cover incorporate oblique locking means for maintaining the system permanently in a locked, unsliding position once the locking push button has been initiated.

In the initiation mechanism, there is provided a spring biased push button and shaft arrangement, wherein the shaft moves longitudinally along its enveloping sleeve until it activates a one-way locking mechanism, while simultaneously biasing the protective cap along the needle until it covers the tip of the needle.

Once the needle tip has been covered, the one-way locking mechanism in both the initiation mechanism and protective cover engage, preventing any subsequent needle stick or re-use.

It is therefore an object of the present invention to provide a system for preventing needle stick which incorporates redundant protective cover locking means.

It is another object of the present invention to provide a system for preventing needle stick wherein there is included a side mounted, push-button initiation system incorporating a longitudinal migrating shaft and enveloping sheath for urging a protective cap along a needle, covering it.

It is another object of the present invention to provide a system for preventing needle stick, wherein there is implemented a protective sheath or cover for the needle which permanently locks in place once it slides over the tip of the needle.

Lastly, it is an object of the present invention to provide a system for preventing needle stick or the like, which is inexpensive, reliable, and safe to implement and utilize.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 4 is a partially cut-away, side view of the embodiment of FIG. 1, illustrating in particular the initiation mechanism and needle cap or sheath after activation, and in the locked capping configuration.

FIG. 5 is a cut-away, enlarged view of the locking apparatus of the initiation mechanism of the embodiment of FIG. 1, illustrating the locking mechanism and system after activation, and in the locked configuration.

DETAILED DESCRIPTION OF THE PREFERRED, EXEMPLARY EMBODIMENT(S)

Figure 1:
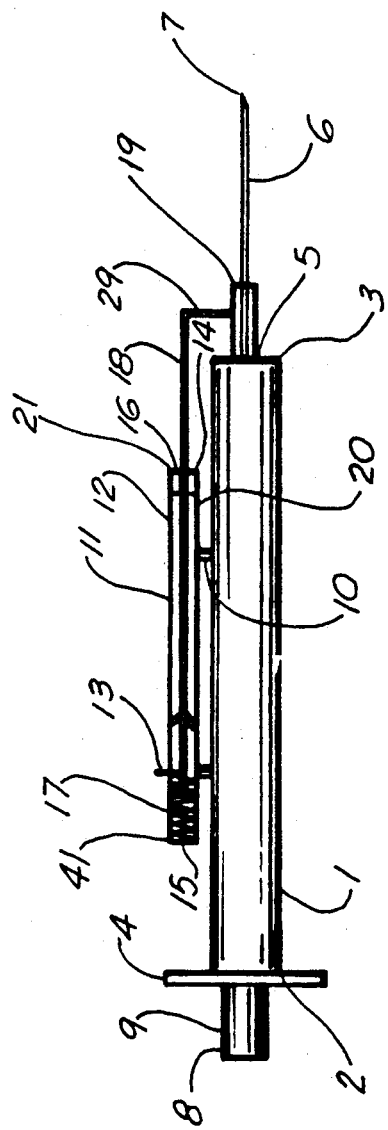
FIG. 1 is a side, partially cut-away view of the preferred embodiment of the safety syringe system of the present invention, illustrating its implementation in conjunction with a plunger syringe and needle.

As can be seen in FIG. 1, the safety syringe system of the preferred, exemplary embodiment of the present invention is designed to be implemented with an off-the-shelf plunger type syringe 1, wherein there is included a cylinder 12 having first (2) and second (3) ends and an outer wall 10, and finger tabs 4 for use in operation. Further included is a plunger 9, in sliding communication with the inner wall of the cylinder 11, the plunger having a push end 8.

Situated at the second end 3 of cylinder 11 is threaded needle connection means 5, to which a needle 6 having a needle point 7 is connected.

Figure 2:
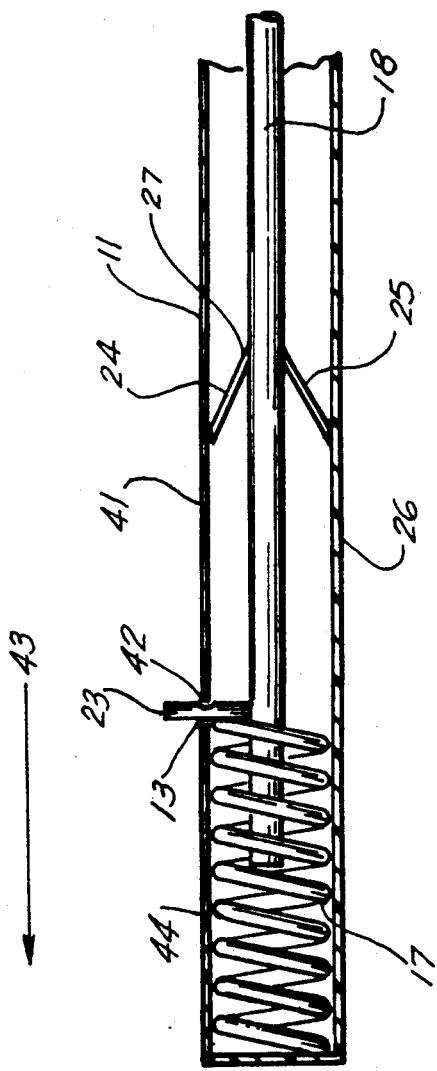
FIG. 2 is a cut-away, enlarged view of the push button area of the initiation mechanism of the embodiment of FIG. 1.

As illustrated in FIGS. 1 and 2, affixed to the lateral, outer side of the syringe body 10 is the locking initiation member 41, comprising a housing 11 having first (15) and second (14) ends, said housing 11 being configured to envelope the shaft 18 in alignment with the longitudinal axis of syringe 1.

Formed in housing 11 at the second end 14 is a shaft aperture 16, from which shaft 18 emanates. Formed on the outer edge of the housing 11, near the first end 15, is a plunger button aperture 13, out of which an activation button 23 protrudes. The activation button 23 is affixed at area 22 to the shaft 18 and is configured for applying lateral bias to the shaft relative to the housing, releasing the activation button 23 from aperture 13, allowing the spring 17 to provide longitudinal force relative to the housing 11, forcing the shaft 18 generally toward the needle point 7. Activation button 23 further includes notch 42 provided in the outer wall of same for communication with housing 11, providing a means of locking the activation button 23 in an uninitiated position, preventing accidental locking of the protective cover over the needle tip.

In the preferred embodiment of the present invention, notch 42 is cut at a right angle, so that in order to initiate activation button 23, the user must apply longitudinal bias 43 to dislocate notch 42 from housing 11, and apply further, lateral pressure 44, fully releasing activation button 23 from aperture 13, allowing shaft 18 to be guided by spring 17 bias in the direction needle tip.

Protruding at an oblique angle 27 from the side of the shaft 18 are locking members 24, 25, set at opposing sides of the shaft. The locking members 24, 25 are configured to communicate with the inner wall 26 of the housing 11 and to space the shaft 18 generally equidistant from the opposing inner side wall 26 of the housing.

Figure 3:
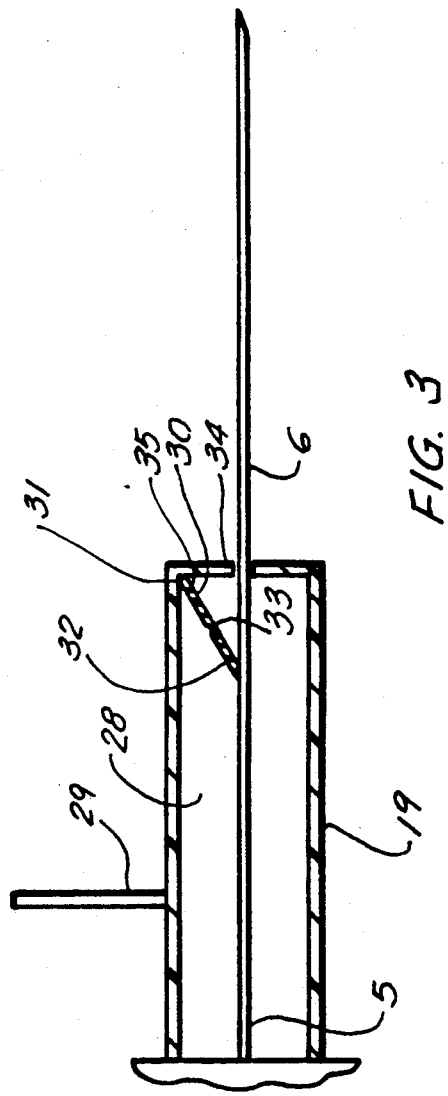
FIG. 3 is a cut-away, enlarged view of the needle cap or sheath of the embodiment of FIG. 1, illustrating the locking mechanism and system prior to activation.

As illustrated in FIGS. 1 and 3, communicating with shaft 18 via lateral shaft extension 29 is a protective cover 19 enveloping the needle 6 about its base, connection area 5, via cylindrical cavity 28, in the systems unprotected configuration, allowing needle 6 and point 7 to be exposed via the needle aperture 34.

A cap locking hatch 30 pliantly extends (note 31) at an oblique angle 35 from the inside wall of the protective cover 19 in communication with the needle 6 via conformed end 32. The cap locking hatch 30 has further formed therein needle tip notch 33, configured for receiving the needle tip or point 7 when the cap is in the closed position, as will be discussed infra.

As shown in FIGS. 2, 4, and 5, once the operator of the syringe has utilized it and wishes to make the syringe un-reusable, the operator merely presses the activation button 23, releasing (note 36) spring 17, allowing it to thrust shaft 18, and thereby the protective cover 19, longitudinally forward 37. This allows the locking members 24, 25 to pass between the first (38) and second (39) locking barriers or a locking ring, locking (note 20) the shaft permanently in the closed position, between barriers 38, 39 or locking the ring and the end wall of the housing 11, acting as a shaft stop 21.

Figure 6:
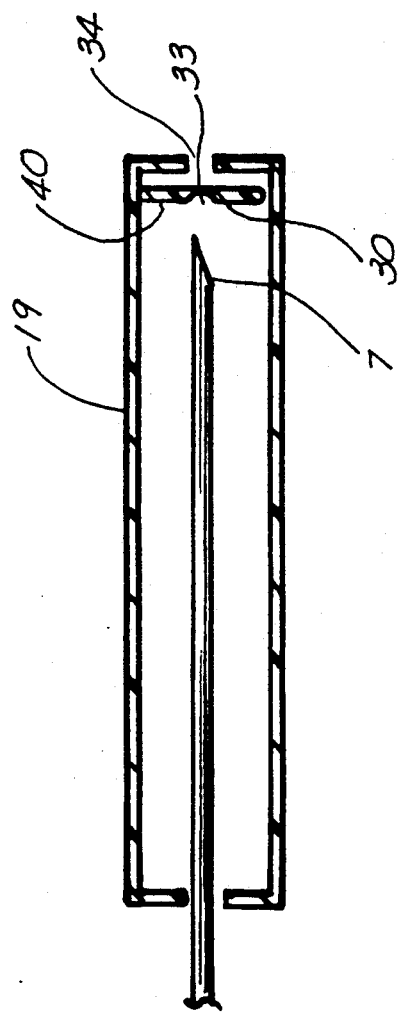
FIG. 6 is a cut-away, enlarged view of the locking apparatus of the initiation mechanism of the embodiment of FIG. 1, illustrating the needle cap or sheath after activation, and in the locked configuration.

Likewise, as shown in FIG. 6, once the aperture 34 of the protective cover 19 has passed the point or tip of the needle 7, the cap locking hatch 30 snaps from its oblique, angled position to a relatively perpendicular angle 40 with respect to the needle and inner side walls of the protective cap 19, preventing access of the needle tip 7 through the aperture 34.

In fact, if the cap 19 were forced against the needle 6, the needle tip 7 would communicate with the needle tip notch 33, preventing the cap locking hatch 30 from bending to allow exposure of the tip.

Once in the locked position, the cap 19 is unalterably, redundantly locked about the needle 6, preventing accidental needle stick and contamination, or subsequent re-use by an addict or other individual.

The embodiment(s) described herein in detail for exemplary purposes are of course subject to many different variations in structure, design, application and methodology. Because many varying and different embodiments may be made within the scope of the inventive concept(s) herein taught, and because many modifications may be made in the embodiment(s) herein detailed in accordance with the descriptive requirements of the law, it is to be understood that the details herein are to be interpreted as illustrative and not in a limiting sense.

What is claimed is:

1. A syringe safety system for preventing accidental needle stick or infection, comprising:
   a syringe having a body comprising first and second ends, inner end outer walls, and a longitudinal axis, a needle having a base and tip, with the base of the needle being in communication with the second end of the body of the syringe;
   a protective cover having inner and outer walls, and first and second ends having needle entrance and egress apertures, respectively, said protective cover being configured to longitudinally envelope the base of the needle in a storage position, and engage and cap the needle tip in an un-reusable configuration after the syringe has been utilized;
   a spring biased, locking push button apparatus configured to urge said protective cover from the storage position to said unreusable configuration upon the pressing of a push button, said locking push button apparatus being anchored to and longitudinally aligned with the body of the syringe, said push button apparatus including
      a housing having first and second ends;
      inner and outer walls forming a cavity therethrough;
      a push button aperture formed generally near said first end of said walls of said housing;
      a locking piece formed about said inner walls generally near said second end;
   said push button apparatus further comprising
      a shaft having
         first and second ends;
         a body configured to communicate with said inner walls of said housing;
         a transversely configured push button, situated generally near said first end of said shaft, said push button being configured to laterally communicate with said push button aperture of said housing; and
         opposing, first and second locking members situated in proximity to said first end of said shaft, said first and second locking members being configured to obliquely communicates with said locking piece of said housing, locking said shaft in position once said locking members have passed through said locking piece;
      bias means associated with said protective cover for urging said shaft in a direction longitudinally aligned with the needle, said bias means being initiated with the application of downward force on said push button of said shaft;
      lateral communication means for connecting said shaft to said protective cover, said lateral communication means transmitting said bias means from said shaft to said protective cover; and a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover.

2. The safety syringe system of claim 1, wherein said cap locking hatch further comprises a needle tip notch configured to envelope the needle tip, should the needle tip come into contact with said cap locking hatch.

3. A syringe safety system for preventing accidental needle stick or infection, comprising:

a syringe having a cylindrical body comprising first and second ends, inner and outer walls, and a longitudinal axis, a needle having a base and top, with the base of the needle being in communication with the second end of the body of the syringe;

a protective cover having inner and outer walls, and first and second ends having needle entrance and egress apertures, respectively, said protective cover being configured to longitudinally envelope the base of the needle in a storage position, and engage and cap the needle tip in an un-reusable configuration after the syringe has been utilized;

a locking push button apparatus configured to urge said protective cover from said storage position to said un-reusable configuration upon the pressing of a push button, said locking push button apparatus being exterior to and longitudinally aligned with the body of the syringe, said push button apparatus including a housing having first and second ends;

inner and outer walls forming a cavity therethrough;

a push button aperture formed generally near said first end of said walls of said housing;

a locking piece formed about said inner walls generally near said second end; said push button apparatus further comprising a shaft having first and second ends;

a body configured to communicate with said inner walls of said housing;

a push button, situated generally near said first end of said shaft, said push button being configured to communicate with said push button aperture of said housing; and opposing, first and second locking members situated in proximity to said first end of said shaft, said first and second locking members being configured in communicate with said locking piece of said housing, said shaft in position once said locking members have passed through said locking piece;

bias means associated with said protective cover for urging said shaft in a direction longitudinally aligned with the needle, said bias means being initiated with the application of downward force on said push button of said shaft;

lateral communication means for connecting said shaft to said protective cover, said lateral communication means transmitting said bias means from said shaft to said protective cover; and a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover.

4. A syringe safety system for preventing accidental needle stick or infection, comprising:

a syringe having a cylindrical body comprising first and second ends, inner and outer walls, and a longitudinal axis, a needle having a base and tip, with the base of the needle being in communication with the second end of the body of the syringe;

a protective cover in longitudinal communication with said needle, said protective cover having inner and outer walls, and first and second ends having needle entrance and egress apertures, respectively, said protective cover being configured to longitudinally envelope the base of the needle in a storage position, and engage and cap the needle tip in an un-reusable configuration after the syringe has been utilized;

bias means associated with said protective cover for urging said protective cover from said storage position to said unreusable configuration, urging said protective cover about the needle, toward the needle tip until said protective cover envelopes the needle tip, said bias means further comprising a shaft having first and second ends, said shaft longitudinally aligned with said syringe means for urging said shaft along a longitudinal path aligned with said syringe, generally toward said syringe tip, said bias means having first and second ends, said first end generally affixed to the cylindrical body of said syringe, said second end generally affixed to said shaft, lateral communication means for connecting said shaft to said protective cover, push button initiation means for selectively initiating said bias means; and a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover.

5. A method of preventing accidental infection comprising the following steps:

(a) providing a syringe safety system, comprising a syringe having a body comprising first and second ends, inner and outer walls, and a longitudinal axis, a needle having a base and tip, with the base of the needle being in communication with the second end of the body of the syringe;

a protective cover having inner and outer walls, and first and second ends having needle entrance and egress apertures, respectively, said protective cover being configured to longitudinally envelope the base of the needle in a storage position, and engage and cap the needle top in an un-reusable configuration after the syringe has been utilized;

a spring biased, locking push button apparatus configured to urge said protective cover from the storage position to said unreusable configuration upon the pressing of a push button, said locking push button apparatus being anchored to and longitudinally aligned with the body of the syringe, said push button apparatus including
a housing having first and second ends;
inner and outer walls forming a cavity therethrough;
a push button aperture formed generally near said first end of said walls of said housing;
a locking piece formed about said inner walls generally near said second end;
said push button apparatus further comprising
a shaft having
first and second ends;
a body configured to communicate with said inner walls of said housing;
a transversely configured push button, situated generally near said first end of said shaft, said push button being configured to laterally communicate with said push button aperture of said housing; and
opposing, first and second locking members situated in proximity to said first end of said shaft, said first and second locking members being configured to obliquely communicate with said locking piece of said housing, locking said shaft in position once said locking members have passed through said locking piece;
bias means associated with said protective cover for urging said shaft in a direction longitudinally aligned with the needle, said bias means being initiated with the application of downward force on said push button of said shaft;
lateral communication means for connecting said shaft to said protective cover, said lateral communication means transmitting said bias means from said shaft to said protective cover; and
a cap locking hatch having first and second ends, said first end being configured to pliantly communicate with said protective cover in proximity to said second end, said cap locking hatch being configured to form a barrier juxtaposed to the needle tip and said egress aperture of said protective cover upon said needle tip being withdrawn into said protective cover;

b. utilizing said syringe to administer a fluid substance; and c. rendering said syringe un-reusable, and lessening the possibility of infection by needle prick from said syringe after use, including the following steps
i. applying downward force on said push button of said shaft,
ii. initiating said bias means, urging said shaft in a direction longitudinally aligned with said needle,
iii. transmitting said bias means from said shaft to said protective cover via said lateral communication means,
iv. slidingly motivating said protective cover from said storage position about said needle towards said needle tip until said protective cover envelopes said needle tip, withdrawing said needle tip from said needle aperture,
v. blocking said needle aperture via said cap locking hatch, and
vi. disposing of said syringe.

6. The method of claim 5, wherein there is included in step "a" the additional step of providing a needle tip notch to said cap locking hatch, said needle tip notch configured to envelope the needle tip should the needle tip come into contact with said cap locking hatch.

7. The method of claim 6, wherein there is further included the step of aligning said needle tip notch of said cap locking hatch in the longitudinal axis of the needle, so that the needle tip notch communicates with the needle tip upon the application of pressure against said protective cover, toward said needle base.

* * * * *